United States Patent
Crawford, Jr. et al.

(10) Patent No.: US 6,399,352 B1
(45) Date of Patent: Jun. 4, 2002

(54) PLANT PORPHOBILINOGEN SYNTHASE AND FUSION PROTEIN THEREOF

(75) Inventors: John Milton Crawford, Jr., Raleigh; John Rice, Pittsboro; Veeresh Sevala, Cary; Sandy Stewart, Durham, all of NC (US)

(73) Assignee: Paradigm Genetics, Inc.

( * ) Notice: Subject to any disclaimer, the term of this patent is extended or adjusted under 35 U.S.C. 154(b) by 0 days.

(21) Appl. No.: 09/741,243

(22) Filed: Dec. 19, 2000

Related U.S. Application Data

(60) Provisional application No. 60/171,785, filed on Dec. 22, 1999.

(51) Int. Cl.$^7$ .............................. C12N 9/88; C12Q 1/527

(52) U.S. Cl. ........................................... 435/232; 435/4

(58) Field of Search ................................. 435/189, 232, 435/4

(56) References Cited

U.S. PATENT DOCUMENTS 5,646,016 A * 7/1997 McCoy et al. ............. 435/69.7

FOREIGN PATENT DOCUMENTS

WO 9516044 6/1995

OTHER PUBLICATIONS

Polking, Gary et al., "A cDNA Clone for 5–Aminolevulinic Acid Dehrydratase from tomato", 107(3):1033–1034, 1995.
Polking, Gary et al., "Characterization of a cDNA encoding 5–aminolevulinic acid dehydratase in tomato", Plant Cell Reports, 4(6):366–369, 1995.
Database WPI, XP002167439.
Boese, Q. et al., "Aminolevulinic Acid Dehrydatase in Pea Pisum–Sativum L. Identification of an Unusual Metal–Binding Domain in the Plant Enzyme", Journal of Biological Chemistry, 266(26):17060–17066, 1991.
Scarponi, L. et al., "Metachlor in corn (Zea mays) and soybean (Glycine max): persistence and biochemical signs of stress during its detoxification", J. Aric. Food Chem., 40(5):884–889, 1992.
Gavel, Y. et al., "A conserved cleavage–site motif in chloroplast transit peptides", Febs Letters, 261(2):455–458, 1990.
Falk, A. et al., "Characterization of a new myrosinase in *Brassica napus*", Plant Molecular Biology, 27:863–874, 1995.

* cited by examiner

*Primary Examiner*—Elizabeth Slobodyansky
(74) *Attorney, Agent, or Firm*—Laura L. Kiefer; Timothy G. Hofmeyer; Deborah H. Spencer

(57) ABSTRACT

Novel DNA and enzymes such as Plant Thioredoxin-Porphobilinogen Synthase (T-PPS) or Plant Porphobilinogen Synthase (PPS), together with novel compositions thereof and methods using such enyzmes are claimed.

8 Claims, No Drawings

PLANT PORPHOBILINOGEN SYNTHASE AND FUSION PROTEIN THEREOF

CROSS-REFERENCE TO RELATED APPLICATIONS

This application claims the benefit of U.S. Provisional Application No. 60/171,785 filed Dec. 22, 1999.

FIELD OF THE INVENTION

The present invention relates to novel enzymes for converting a compound or substrate known as aminolevulinate (ALA) to another compound or product known as prophobilinogen (PBG). The present invention also relates to novel DNA that encodes for such enzymes.

BACKGROUND OF THE INVENTION

Enzymes are important laboratory tools for discovering new agricultural or related compounds such as insecticides, herbicides, fungicides, nematocides, antimicrobials and the like. In plants, there is a key biochemical pathway in which a pyrrole ring-containing compound known as porphobilinogen (PBG) is produced from two acyclic or open-chain molecules known as aminolevulinate (ALA). PBG is a precursor or substrate for both heme and chlorophyll biosynthesis in plants. Plants employ an enzyme that can catalyze or convert ALA to PBG. Unfortunately, this native enzyme cannot be expressed so that it is active in a non-plant host, such as bacteria, since such expressions have been found to yield an insoluble and inactive enzyme. Thus, it became desirable to develop active, plant-based enzymes that could convert aminolevulinate to porophobilinogen and yet still remain soluble under laboratory conditions.

SUMMARY OF THE INVENTION

The present invention advantageously provides an active, plant-based protein or enzymes known as plant thioredoxin-porphobilinogen synthase (T-PPS) and plant porphobilinogen synthase (PPS) that can convert aminolevulinate to porophobilinogen and yet still remain soluble under laboratory conditions. The present invention has the further advantage of also providing DNA in a non-natural host such as bacteria, virus, yeast, etc. that will produce the desired protein or functional fragments thereof, outside of its native plant source.

Accordingly, in one embodiment, the present invention is directed toward DNA or polynucleotide characterized by a) SEQ ID NOs: 1 or 7;

b) the complementary sequence thereof; or c) the double stranded sequence of a) and b).

In a second embodiment, the present invention is directed towards DNA or polynucleotide characterized in that its homology to the sequence as shown in SEQ ID NOs: 1 or 7 is at least 80%. Preferably, the DNA or polynucleotide is characterized in that its homology to the sequence as shown in SEQ ID NOs: 1 or 7 is at least 90%.

In a third embodiment, the present invention is directed towards DNA or polynucleotide that encodes the total: or functional fragments of an amino acid sequence as shown in SEQ ID NOs: 2 or 8.

In a fourth embodiment, the present invention is directed towards RNA characterized in that it is complementary to the DNA of SEQ ID NOs: 1 or 7.

In a fifth embodiment, the present invention is directed towards an expression construct, characterized in that it encompasses DNA or polynucleotide described in the first, second or third embodiments and a sequence that is functionally linked thereto that allows the DNA or polynucleotide to be expressed.

In a sixth embodiment, the present invention is directed towards a plasmid characterized in that it contains DNA or polynucleotide described in the first, second or third embodiments.

In a seventh embodiment, the present invention is directed towards a protein or polypeptide represented by SEQ ID NO: 2, known herein as "Plant Thioredoxin-Porphobilinogen Synthase" (T-PPS) or a protein represented by SEQ ID NO: 8, known as "Plant Porphobilinogen Synthase" (PPS). Preferably, the protein is in a buffered composition.

In an eight embodiment, the present invention is directed towards a method of determining the enzymatic activity of the protein or polypeptide of SEQ ID NO: 2 (i.e. plant thioredoxin-porphobilinogen synthase) or SEQ ID NO: 8 (i.e. plant porphobilinogen synthase), characterized by contacting or converting δ-aminolevulinic acid (a substrate) with said protein and measuring the amount of porphobilinogen (a product) formed therefrom. Preferably, the protein is in a buffered composition.

In a ninth embodiment, the present invention is directed toward a method of identifying a compound which can modify the activity of the protein or polypeptide of SEQ ID NOs: 2, 8 or a functional fragment thereof comprising contacting or converting δ-aminolevulinic acid with said protein or polypeptide or a functional fragment thereof in the presence of a test compound and measuring the amount of porphobilinogen formed therefrom. Preferably, the protein or polypeptide is in a buffered composition. Also preferred is that said identified compound inhibits said protein or polypeptide or functional fragment thereof.

In a tenth embodiment, the present invention is directed towards a method of inhibiting plant growth comprising applying to a plant a compound which inhibits the enzymatic activity of plant thioredoxin-porphobilinogen synthase or plant porphobilinogen synthase. Preferably, the protein or polypeptide is in a buffered composition.

DETAILED DESCRIPTION OF THE INVENTION

The present invention will now be described more fully hereinafter with reference to the accompanying figures or drawings, in which preferred embodiments of the invention are shown. This invention may, however, be embodied in different forms and should not be construed as limited to the embodiments set forth herein. Rather, these embodiments are provided so that this disclosure will be thorough and complete, and will fully convey the scope of the invention to those skilled in the art.

The invention also relates to the use of substances which are found with the aid of the above-described method for use as herbicides.

"Buffer" or "buffered composition" refers to a solution in which a buffering agent has been added and which tends to prevent or resist rapid changes in pH upon the addition of small quantities of acid or base.

"Chemically synthesized," as related to a sequence of DNA, means that the component nucleotides are assembled in vitro. Manual chemical synthesis of DNA may be accomplished using well established techniques in the art.

"Complementary" relates to the capability of purine and pyrimidine nucleotides to form base pairs with each other via hydrogen bonds. Complementary base pairs are, inter alia, guanine and cytosine, adenine and thymine, and adenine and uracil.

"DNA" or "polynucleotide" refers to deoxyribonucleic acid.

"Expression" or "expressing" refers to the transcription and/or in the case of a protein gene product, translation, of a heterologous or homologous gene to yield the gene product encoded by the structural portion of the gene or DNA fragment.

"Expression construct" refers to the union of a functional fragment in a plasmid, resulting in a vector that is capable of expressing the functional fragment.

"Functional fragments" describes those DNA fragments which encode for plant porphobilinogen synthase or the fusion protein thereof, or a polypeptide portion therof that still maintains a substantial amount of the activity or function of the plant porphobilinogen synthase or the fusion protein thereof.

"Fusion protein" refers to a chimeric protein or polypeptide in which plant porphobilinogen synthase or functional fragment thereof, is joined to a second protein or polypeptide such as thioredoxin, maltose binding protein, or other proteins. The second protein or polypeptide serves the function of helping or enhancing the solubility and/or the post-translational modification of the plant porphobilinogen synthase or functional fragment thereof.

"Gene" refers to a unit composed of a promoter region, a structural gene region and a transcription termination region.

"Gene product" refers to a specific protein or RNA product derived from the structural portion of the gene.

"Heterologous" is used to indicate that a nucleic acid sequence (e.g., a gene) or a protean has a different natural origin or source with respect to its current host. Heterologous is also used to indicate that one or more of the domains present in a protein differ in their natural origin with respect to other domains present. In cases where a portion of a heterologous gene originates from a different organism the heterologous gene is also known as a chimera.

"Homologous" is used to indicate that a nucleic acid sequence (e.g. a gene) or a protein has a similar or the same natural origin or source with respect to its current host.

"Homology" in relation to DNA means that DNA segments which are at least 15 base pairs long or strands which are complementary to the DNA match the corresponding DNA in at least 80%, preferably in 90%, of the nucleotides. Such a homology is determined, inter alia, with the aid of computer programs such as the GCG program (Devereux et al. (1983), Nucleic Acids Res. 12, 3 87–395). Homology also exists when a DNA segment is capable of hybridizing with the DNA strand in question or with its complementary strand.

"Hybridization" or "to hybridize" describes the process in which a single stranded nucleic acid molecule undergoes base pairing with a complementary DNA strand, where the capability of a single-stranded nucleic acid molecule depends on the stringency of the hybridization conditions.

"Nucleic acid sequence" as used herein refers to a nucleotide, oligonucleotide, or polynucleotide, and fragments thereof, and to DNA or RNA of genomic or synthetic origin which may be single- or double-stranded, and which may represent a sense or antisense strand.

"Plasmid" refers to an circular, autonomous (i.e. self-replicating) extrachromosomal genetic element. The original plasmids used for the present invention are either commercially available or freely accessible or can be derived from such plasmids by known methods.

The terms "protein" or "polypeptide" are to be regarded as substantially equivalent.

"RNA" refers to ribonucleic acid.

"Stringency" relates to the hybridization conditions. "High stringency makes base pairing difficult. To do this, high temperatures of 42° C. or less are used, a formamide concentration of less than 20% and low salt (SSC) concentrations, Alternatively, temperatures of 65° C. or less can be used in combination with a low salt concentration (SSPE). "Low stringency" conditions favor the formation of base pairs. The temperatures used here are 37° C. or less, the formamide concentration is less than 50%, and the salt concentration (SSC) is moderate. Alternatively, temperatures of 50° C. or less in combination with a medium to high salt concentration (SSPE) are used.

"Vector" describes a DNA vehicle used for introducing exogenous DNA into host cells. A vector contains a nucleotide sequence which encodes one or more polypeptides or proteins. For example, a plasmid is an example of a circular vector.

One skilled in the art is aware of the fact that the degenerate genetic code (i.e. 64 codons encode 20 amino acids) allow a large number of "silent" substitutions of nucleotide base pairs to be introduced into the sequence shown here without changing the identity of the protein products encoded by it. The scope of the invention includes all such substitutions.

DNA Isolation

The DNA or nucleic acid mentioned here can exist in complete cells, in cell lysates, in partially purified or biologically pure form, i.e. when other cell components or chemical precursors and by-products, in the case of chemical DNA synthesis, have been removed.

The DNA mentioned here can be obtained by a series of genetic and recombinant DNA techniques, for example by means of amplification with the aid of the polymerase chain reaction (PCR) or else by de novo DNA synthesis. The DNA mentioned here can be isolated by means of RT-PCR amplification of total RNA from suitable plant cells using oligonucleotide or polynucleotide primers which are directed at a suitable region of SEQ ID NOs: 1 or 7 (see, for example, J. Sambrook et al, (1989), Molecular Cloning, 2nd edition, chapter 14).

Expressing and purifying the protein

The invention also relates to proteins or functional fragments thereof which have plant porphobilinogen synthase activity and which are encoded by an above-described DNA.

The skilled worker knows that the proteins of the present invention can be obtained by various routes, for example by chemical methods such as the solid-phase method. To obtain larger quantities of protein, the use of recombinant methods is recommended. Expression of a cloned plant porphobilinogen synthase gene or fragments thereof can take place in a series of suitable host cells which are known to the skilled worker. To this end, a plant porphobilinogen synthase gene is introduced into a host cell with the aid of known methods.

The integration of the cloned plant porphobilinogen synthase gene in the chromosome of the host cell is within the scope of the present invention. Preferably, the gene or functional fragments thereof are inserted into a plasmid, and the encoding regions of the plant porphobilinogen synthase gene or fragments thereof are functionally linked to a constitutive or inducible promoter.

The basic steps for generating the recombinant plant porphobilinogen synthase are:
1. Obtaining a natural, synthetic or semi-synthetic DNA that can express plant porphobilinogen synthase.

2. Introducing this DNA into an expression vector which is suitable for expressing plant porphobilinogen synthase either alone or as a fused protein.
3. Transformation of a suitable host cell, preferably a prokaryotic host cell, with this expression vector.
4. Growing this transformed host cell in a manner which is suitable for expressing plant porphobilinogen synthase.
5. Harvesting the cells and purifying plant porphobilinogen synthase by suitable known methods.

The encoding regions of plant porphobilinogen synthase can be expressed by the customary methods in *E. coli*, either separately or together. Suitable expression systems for *E. coli* are commercially available, for example, the plasmids of the pET series, for example pET3a, pET23a, pET28a with HIS-Tag or pET32a with HIS-Tag for the simple purification and thioredoxin fusion for improving the solubility of the expressed enzyme, and pGEX with glutathion synthetase fusion plasmids are transformed into XDE3-lysogenic *E. coli* strains, for example. BL21(DE3), HMS 174(DE3) or AD494(DE3). Expression is induced with IPTG under standard conditions known to the skilled worker. After cell induction, incubation is carried out for 3 to 24 hours at temperatures from about 18° C. to about 37° C. The cells are disrupted by sonication in disruption buffer (10 to 200 mM tricine, 100 to 500 mM NaCl, pH 5 to 8). The protein which has been expressed can be purified by chromatographic methods, in the case of protein which has been expressed with a his-Tag by means of chromatography on an Ni—NTA column.

Alternatively, the proteins may also be expressed in plants.

EXAMPLE 1

Preparation of DNA Coding Sequence for Recombinant Plant Thioredoxin-porphobilinogen Synthase Total RNA is collected from 8–10 day old tomato (*Lycopersicon esculentum*) fruit using published protocols and reagents (Trizol) from Life Technologies, Inc. (Rockville, Md.). Polynucleotide primers are designed and employed such that their use in polymerase chain reaction (PCR) generates a truncated form of the plant porphobilinogen synthase gene from tomato (*Lycopersicon esculentum*) total RNA. One hundred nanograms each of custom polynucleotide primers, TTATTCTCGAGTTAC-CTCTTCTCTCCACACAGG (SEQ ID NO: 5) and TATTA-GAATTCGCTAGCAAGGAAGGGCATGA (SEQ: ID NO: 6), are incubated with 1 microgram of total RNA in a reverse transcriptase polymerase chain reaction (RT-PCR) kit (Life Technologies) according to the manufacturer's recommendations.

The resulting PCR product (i.e. plant porphobilinogen synthase DNAs) and plasmid pET32b(+) (Novagen, Madison, Wis.), are digested with restriction endonucleases EcoR I and Xho I, as directed by the manufacturer (Life Technologies) to give two linear proteins. Plasmid pET32b (+) contains DNA (SEQ ID NO: 3) which encodes for the thioredoxin (trxA) protein fragment (SEQ ID NO: 4). Thioredoxin is a functional fragment of the pET32b(+), plasmid and has 501 nucleotide base pairs. This portion is joined to the PPS functional fragment such that the last base, i.e. 501, of trxA is attached to the first base, i.e. 1, of PPS. This union creates a novel DNA capable of encoding a thioredoxin-PPS fusion protein. Ligation of these two linear DNAs with DNA T4 ligase produces the recombinant clone plant porphobilinogen synthase pET32b(+) (Life Technologies). DNA sequence analysis verifies the integrity of the plant thioredoxin-porphobilinogensynthase/ pET32b (+) clone containing DNA that encodes for plant thioredoxin-porphobilinogen synthase (SEQ ID NOs: 1 and 2), a fisio n protein.

EXAMPLE 2

Preparation of Plant Thioredoxin-Porphobilinogen Synthase (T-PPS)

Cloned plant thioredoxin-porphobilinogen synthase/ pET32b(+) is transformed into a proprietary bacterial strain, *E. coli* AD)494(DE3)lysS (Novagen Inc., Madison, Wis.), according to the manufacturer's instructions. Transcription and translation of plant thioredoxin-porphobilinogen synthase/pET32b(+) in this host requires the sugar, isopropylthio-beta-galactoside (IPTG). Transformed bacteria are grown in LB liquid media (10 grams each tryptone and NaCl; 5 grams yeast extract; $H_2O$ to one liter) at 37° C. to an optical density of 0.6 at 600 nm. At that point, IPTG is added to a final concentration of 1 millimolar and the culture is incubated at 37° C. for 4 additional hours. Bacteria are pelleted via centrifugation, the supernatant discarded, and the pellet is frozen to −80° C. Pellets are resuspended in 100 millimolar tricine buffer, pH 7.9; 300 millimolar NaCl or other suitable biochemical buffer, mechanically disrupted, and centrifuged. Four hours post IPTG induction, soluble plant thioredoxin-porphobilinogen synthase protein (SEQ ID NO: 2) is detectable in the collected supernatant, as determined by western blot analysis, which is targeted to the attached HIS sequence, thirodoxin, or the S-tag portion of the protein product.

EXAMPLE 3

Testing Enzyme Activity of Plant Thioredoxin-porphobilinogen Synthase

Enzyme activity is tested in accordance with EC 4.2.1.24 using the following assay principle:

[Reaction scheme showing two molecules of aminolevulinate (HOOC-CH2-CH2-C(=O)-CH2-NH2) reacting via Enzyme to form Porphobilinogen (pyrrole ring with NH2-CH2-, COOH-CH2-, and -CH2-CH2-COOH substituents) + 2H2O]

Aminolevulinate

Porphobilinogen

The enzyme activity of plant thioredoxin-porphobilinogen synthase (T-PPS) is measured as porphobilinogen (PBG) formation from δ-aminolevulinic acid (Aminolevulinate or ALA). A typical reaction is as follows: the reaction is carried out at 37° C. for 1 hour in Tricine buffer pH 7.9 or other suitable biochemical buffer, 2.5 mM ALA, 5 mM $MgCl_2$ and 1.25 μg of purified recombinant protein from E. coli expression system in a final assay volume of 100 μl. PBG is quantified spectrophotometrically after reaction with the 100 μl Ehrlich's reagent solution. Optical density is determined after 60 minutes at 555 nm. This assay indicates that plant thioredoxin-porphobilinogen synthase is active, i.e. plant thioredoxin-porphobilinogen synthase can convert ALA to PBG.

EXAMPLE 4

Using Assay to Identify Inhibitory or Herbicidal Compounds

Essentially the same procedure as described in Example 3 is performed, except that a test compound is added to or mixed with the plant thioredoxin-porphobilinogen synthase prior to addition of δ-aminolevulinic acid. A decrease in product (i.e. PBG) compared to the control would indicate that the test compound is an inhibitor of plant thioredoxin-porphobilinogen synthase.

EXAMPLE 5

Preparation of DNA Encoding Sequence for Plant Porphobilinogen Synthase (PPS)

Essentially the same procedures are employed as described in Example 1, except that the plasmid pET-30b(+) (Novagen Inc., Madison, Wis.) is used in place of plasmid pET32b(+) to give a plant porphobilinogen synthase/pET-30b(+) clone that contains the DNA coding sequence for plant porphobilinogen synthase (PPS) (SEQ ID NO: 7).

EXAMPLE 6

Preparation of Plant Porphobilinogen Synthase (PPS)

The same procedures are employed as described in Example 2, except that the plant porphobilinogen synthase/pET-30b(+) of Example 5 is used in place of plant thioredoxin-porphobilinogen synthase/pET32b(+), to give the desired plant porphobilinogen synthase (SEQ ID NO: 8).

EXAMPLE 7

Testing Enzyme Activity of Plant Porphobilinogen Synthase

The same procedures are employed as described in Example 3, except that the plant porphobilinogen synthase of Example 5 is used in place of plant thioredoxin-porphobilinogen synthase.

EXAMPLE 8

Using Assay to Identify Inhibitory or Herbicidal Compounds

The same procedures are employed as described in Example 4, except that the plant porphobilinogen synthase of Example 5 is used in place of plant thioredoxin-porphobilinogen synthase.

What is claimed is:

1. The purified polypeptide of SEQ ID NO: 2 or an enzymatically active fragment thereof.

2. The purified polypeptide of SEQ ID NO: 8 or an enzymatically active fragment thereof.

3. The purified polypeptide of SEQ ID NOs: 2 or 8 in a buffer.

4. Method of determining the enzymatic activity of the polypeptide of SEQ ID NOs: 2 or 8 or an enzymatically active fragment thereof, comprising contacting δ-aminolevulinic acid with said polypeptide or said enzymatically active fragment thereof and measuring the amount of porphobilinogen formed therefrom.

5. The method of claim 4 wherein said polypeptide is in a buffer.

6. Method of identifying a compound which can modify the enzymatic activity of the polypeptide SEQ ID NOs: 2, 8 or an enzymatically active fragment thereof, comprising contacting δ-aminolevulinic acid with said polypeptide or said enzymatically active fragment thereof in the presence of the test compound and measuring the amount of porphobilinogen formed therefrom.

7. The method of claim 6 wherein said polypeptide is in a buffer.

8. The method of claim 7 wherein said identified compound inhibits said polypeptide or said enzymatically active fragment thereof.

* * * * *

SEQUENCE LISTING

<160> NUMBER OF SEQ ID NOS: 8

<210> SEQ ID NO 1
<211> LENGTH: 1653
<212> TYPE: DNA
<213> ORGANISM: Artificial Sequence
<220> FEATURE:
<223> OTHER INFORMATION: DNA encoding a plant
      thioredoxin-porphobilinogen synthase fusi on protein

<400> SEQUENCE: 1

```
atgagcgata aaattattca cctgactgac gacagttttg acacggatgt a ctcaaagcg      60 gacggggcga tcctcgtcga tttctgggca gagtggtgcg gtccgtgcaa a atgatcgcc     120 ccgattctgg atgaaatcgc tgacgaatat cagggcaaac tgaccgttgc a aaactgaac     180 atcgatcaaa accctggcac tgcgccgaaa tatggcatcc gtggtatccc g actctgctg     240 ctgttcaaaa acggtgaagt ggcggcaacc aaagtgggtg cactgtctaa a ggtcagttg     300 aaagagttcc tcgacgctaa cctggccggt tctggttctg gccatatgca c catcatcat     360 catcattctt ctggtctggt gccacgcggt tctggtatga agaaaccgc t gctgctaaa      420 ttcgaacgcc agcacatgga cagcccagat ctgggtaccg acgacgacga c aaggccatg     480 gctgatatcg gatccgaatt cgctagcaag gaagggcatg ataatgggtc t agctcaggg     540 cccttgagaa agatggggtt gactgatgag gagtgtgagg ctgctgtagt t gccggaaat     600 gtacctgaag ctcctccggt tccaccaaag ccggctgcac ctgacggtac c cctattgtg     660 tcttcactgc caattaatag gagaccacgc cgtaatcgta ggtcgtcagc a gcaagagct     720
```

-continued

| | |
|---|---|
| gcattccagg aaacaaatat aagccctgca aatcttgtat atccactatt t attcatgag | 780 |
| ggtgaagagg acacacctat tggagcaatg cctggatgtt ataggcttgg a tggaggcat | 840 |
| ggtcttgttg aagaggtcgc aaaggcaagg gatgttggag tcaacagcat t gtgctcttc | 900 |
| ccaaaagttc cagatgcttt aaagacctct acaggagatg aagcttacaa t gacaatgga | 960 |
| ttagtgcccc gaacaatacg tttgctgaaa gacaaatacc ctgatcttgt t atctacact | 1020 |
| gatgttgctt tggatccata ttcatctgat gggcatgatg gcattgtgag a gaagatgga | 1080 |
| gttatcatga atgacgagac tgtgcatcag ttgtgcaaac aggcagttgc t caggccaga | 1140 |
| gcaggagcag atgttgtcag tccaagtgac atgatggatg gtcgtgtcgg a gcaattcga | 1200 |
| gcagctcttg atgctgaagg atttcagcat gtgtcaatca tgtcatatac g gcaaagtat | 1260 |
| gcaagctcct tttatggacc tttcagagag gctttagatt caaatccacg t tttggggat | 1320 |
| aagaaaactt atcagatgaa ccccgcaaat tacagagaag cattagttga g atgcaagca | 1380 |
| gatgagtctg aaggagctga tattcttctt gttaaaccag gtttgcctta t ttggatatt | 1440 |
| attaggcttc ttcgggataa atctcctttg cccatagctg cctatcaggt t caggtgaa | 1500 |
| tactcgatga tcaaagcagg tggggttcta aaaatgatcg atgaagaaag g gttatgatg | 1560 |
| gaatcattga tgtgccttcg acgagctggt gctgacataa ttttgaccta t tttgctctg | 1620 |
| caagccggta gatgcctgtg tggagagaag agg | 1653 |

<210> SEQ ID NO 2
<211> LENGTH: 551
<212> TYPE: PRT
<213> ORGANISM: Artificial Sequence
<220> FEATURE:
<223> OTHER INFORMATION: A plant thioredoxin-porph obilinogen synthase
      fusion protein

<400> SEQUENCE: 2

```
Met Ser Asp Lys Ile Ile His Leu Thr Asp A sp Ser Phe Asp Thr Asp
  1               5                  10                  15

Val Leu Lys Ala Asp Gly Ala Ile Leu Val A sp Phe Trp Ala Glu Trp
             20                  25                  30

Cys Gly Pro Cys Lys Met Ile Ala Pro Ile L eu Asp Glu Ile Ala Asp
         35                  40                  45

Glu Tyr Gln Gly Lys Leu Thr Val Ala Lys L eu Asn Ile Asp Gln Asn
     50                  55                  60

Pro Gly Thr Ala Pro Lys Tyr Gly Ile Arg G ly Ile Pro Thr Leu Leu
 65                  70                  75                  80

Leu Phe Lys Asn Gly Glu Val Ala Ala Thr L ys Val Gly Ala Leu Ser
                 85                  90                  95

Lys Gly Gln Leu Lys Glu Phe Leu Asp Ala A sn Leu Ala Gly Ser Gly
            100                 105                 110

Ser Gly His Met His His His His His His S er Ser Gly Leu Val Pro
        115                 120                 125

Arg Gly Ser Gly Met Lys Glu Thr Ala Ala A la Lys Phe Glu Arg Gln
    130                 135                 140

His Met Asp Ser Pro Asp Leu Gly Thr Asp A sp Asp Asp Lys Ala Met
145                 150                 155                 160

Ala Asp Ile Gly Ser Glu Phe Ala Ser Lys G lu Gly His Asp Asn Gly
                165                 170                 175

Ser Ser Ser Gly Pro Leu Arg Lys Met Gly L eu Thr Asp Glu Glu Cys
            180                 185                 190
```

```
Glu Ala Ala Val Val Ala Gly Asn Val Pro Glu Ala Pro Pro Val Pro
            195                 200                 205

Pro Lys Pro Ala Ala Pro Asp Gly Thr Pro Ile Val Ser Ser Leu Pro
        210                 215                 220

Ile Asn Arg Arg Pro Arg Arg Asn Arg Arg Ser Ser Ala Ala Arg Ala
225                 230                 235                 240

Ala Phe Gln Glu Thr Asn Ile Ser Pro Ala Asn Leu Val Tyr Pro Leu
                245                 250                 255

Phe Ile His Glu Gly Glu Asp Thr Pro Ile Gly Ala Met Pro Gly
            260                 265                 270

Cys Tyr Arg Leu Gly Trp Arg His Gly Leu Val Glu Glu Val Ala Lys
            275                 280                 285

Ala Arg Asp Val Gly Val Asn Ser Ile Val Leu Phe Pro Lys Val Pro
        290                 295                 300

Asp Ala Leu Lys Thr Ser Thr Gly Asp Glu Ala Tyr Asn Asp Asn Gly
305                 310                 315                 320

Leu Val Pro Arg Thr Ile Arg Leu Leu Lys Asp Lys Tyr Pro Asp Leu
                325                 330                 335

Val Ile Tyr Thr Asp Val Ala Leu Asp Pro Tyr Ser Ser Asp Gly His
            340                 345                 350

Asp Gly Ile Val Arg Glu Asp Gly Val Ile Met Asn Asp Glu Thr Val
            355                 360                 365

His Gln Leu Cys Lys Gln Ala Val Ala Gln Ala Arg Ala Gly Ala Asp
        370                 375                 380

Val Val Ser Pro Ser Asp Met Met Asp Gly Arg Val Gly Ala Ile Arg
385                 390                 395                 400

Ala Ala Leu Asp Ala Glu Gly Phe Gln His Val Ser Ile Met Ser Tyr
                405                 410                 415

Thr Ala Lys Tyr Ala Ser Ser Phe Tyr Gly Pro Phe Arg Glu Ala Leu
            420                 425                 430

Asp Ser Asn Pro Arg Phe Gly Asp Lys Lys Thr Tyr Gln Met Asn Pro
        435                 440                 445

Ala Asn Tyr Arg Glu Ala Leu Val Glu Met Gln Ala Asp Glu Ser Glu
    450                 455                 460

Gly Ala Asp Ile Leu Leu Val Lys Pro Gly Leu Pro Tyr Leu Asp Ile
465                 470                 475                 480

Ile Arg Leu Leu Arg Asp Lys Ser Pro Leu Pro Ile Ala Ala Tyr Gln
                485                 490                 495

Val Ser Gly Glu Tyr Ser Met Ile Lys Ala Gly Gly Val Leu Lys Met
            500                 505                 510

Ile Asp Glu Glu Arg Val Met Met Glu Ser Leu Met Cys Leu Arg Arg
        515                 520                 525

Ala Gly Ala Asp Ile Ile Leu Thr Tyr Phe Ala Leu Gln Ala Gly Arg
    530                 535                 540

Cys Leu Cys Gly Glu Lys Arg
545                 550

<210> SEQ ID NO 3
<211> LENGTH: 501
<212> TYPE: DNA
<213> ORGANISM: Unknown
<220> FEATURE:
<223> OTHER INFORMATION: DNA encoding thioredoxin functional fragment

<400> SEQUENCE: 3
```

-continued

```
atgagcgata aaattattca cctgactgac gacagttttg acacggatgt a ctcaaagcg    60 gacgggcga tcctcgtcga tttctgggca gagtggtgcg gtccgtgcaa a atgatcgcc   120 ccgattctgg atgaaatcgc tgacgaatat cagggcaaac tgaccgttgc a aaactgaac   180 atcgatcaaa accctggcac tgcgccgaaa tatggcatcc gtggtatccc g actctgctg   240 ctgttcaaaa acggtgaagt ggcggcaacc aaagtgggtg cactgtctaa a ggtcagttg   300 aaagagttcc tcgacgctaa cctggccggt tctggttctg gccatatgca c catcatcat   360 catcattctt ctggtctggt gccacgcggt tctggtatga agaaaccgc t gctgctaaa   420 ttcgaacgcc agcacatgga cagcccagat ctgggtaccg acgacgacga c aaggccatg   480 gctgatatcg gatccgaatt c                                             501
```

<210> SEQ ID NO 4
<211> LENGTH: 167
<212> TYPE: PRT
<213> ORGANISM: Unknown
<220> FEATURE:
<223> OTHER INFORMATION: Thioredoxin functional fr agment

<400> SEQUENCE: 4

```
Met Ser Asp Lys Ile Ile His Leu Thr Asp Ser Phe Asp Thr Asp
 1               5                  10                  15

Val Leu Lys Ala Asp Gly Ala Ile Leu Val Asp Phe Trp Ala Glu Trp
                20                  25                  30

Cys Gly Pro Cys Lys Met Ile Ala Pro Ile Leu Asp Glu Ile Ala Asp
            35                  40                  45

Glu Tyr Gln Gly Lys Leu Thr Val Ala Lys Leu Asn Ile Asp Gln Asn
        50                  55                  60

Pro Gly Thr Ala Pro Lys Tyr Gly Ile Arg Gly Ile Pro Thr Leu Leu
65                  70                  75                  80

Leu Phe Lys Asn Gly Glu Val Ala Ala Thr Lys Val Gly Ala Leu Ser
                85                  90                  95

Lys Gly Gln Leu Lys Glu Phe Leu Asp Ala Asn Leu Ala Gly Ser Gly
           100                 105                 110

Ser Gly His Met His His His His His Ser Ser Gly Leu Val Pro
           115                 120                 125

Arg Gly Ser Gly Met Lys Glu Thr Ala Ala Ala Lys Phe Glu Arg Gln
       130                 135                 140

His Met Asp Ser Pro Asp Leu Gly Thr Asp Asp Asp Asp Lys Ala Met
145                 150                 155                 160

Ala Asp Ile Gly Ser Glu Phe
                165
```

<210> SEQ ID NO 5
<211> LENGTH: 33
<212> TYPE: DNA
<213> ORGANISM: Artificial Sequence
<220> FEATURE:
<223> OTHER INFORMATION: Oligonucleotide primer

<400> SEQUENCE: 5

```
ttattctcga gttacctctt ctctccacac agg                                 33
```

<210> SEQ ID NO 6
<211> LENGTH: 31
<212> TYPE: DNA
<213> ORGANISM: Artificial Sequence
<220> FEATURE:

<223> OTHER INFORMATION: Oligonucleotide primer

<400> SEQUENCE: 6
tattagaatt cgctagcaag gaagggcatg a    31

<210> SEQ ID NO 7
<211> LENGTH: 1152
<212> TYPE: DNA
<213> ORGANISM: Lycopersicon esculentum
<220> FEATURE:

<400> SEQUENCE: 7

```
gctagcaagg aagggcatga taatgggtct agctcagggc ccttgagaaa g atggggttg      60
actgatgagg agtgtgaggc tgctgtagtt gccggaaatg tacctgaagc t cctccggtt    120
ccaccaaagc cggctgcacc tgacggtacc cctattgtgt cttcactgcc a attaatagg    180
agaccacgcc gtaatcgtag gtcgtcagca gcaagagctg cattccagga a acaaatata    240
agccctgcaa atcttgtata tccactattt attcatgagg gtgaagagga c acacctatt    300
ggagcaatgc ctggatgtta taggcttgga tggaggcatg gtcttgttga a gaggtcgca    360
aaggcaaggg atgttggagt caacagcatt gtgctcttcc caaaagttcc a gatgcttta    420
aagacctcta caggagatga agcttacaat gacaatggat tagtgccccg a acaatacgt    480
ttgctgaaag acaaataccc tgatcttgtt atctacactg atgttgcttt g gatccatat    540
tcatctgatg ggcatgatgg cattgtgaga aagatggatt tatcatgaa t gacgagact    600
gtgcatcagt tgtgcaaaca ggcagttgct caggccagag caggagcaga t gttgtcagt    660
ccaagtgaca tgatggatgg tcgtgtcgga gcaattcgag cagctcttga t gctgaagga    720
tttcagcatg tgtcaatcat gtcatatacg gcaaagtatg caagctcctt t tatggacct    780
ttcagagagg ctttagattc aaatccacgt tttggggata agaaaactta t cagatgaac    840
cccgcaaatt acagagaagc attagttgag atgcaagcag atgagtctga a ggagctgat    900
attcttcttg ttaaaccagg tttgccttat ttggatatta ttaggcttct t cgggataaa    960
tctcctttgc ccatagctgc ctatcaggtt tcaggtgaat actcgatgat c aaagcaggt   1020
ggggttctaa aaatgatcga tgaagaaagg gttatgatgg aatcattgat g tgccttcga   1080
cgagctggtg ctgacataat tttgacctat tttgctctgc aagccggtag a tgcctgtgt   1140
ggagagaaga gg                                                        1152
```

<210> SEQ ID NO 8
<211> LENGTH: 384
<212> TYPE: PRT
<213> ORGANISM: Lycopersicon esculentum

<400> SEQUENCE: 8

Ala Ser Lys Glu Gly His Asp Asn Gly Ser S er Ser Gly Pro Leu Arg
1               5                   10                  15

Lys Met Gly Leu Thr Asp Glu Glu Cys Glu A la Ala Val Val Ala Gly
            20                  25                  30

Asn Val Pro Glu Ala Pro Pro Val Pro Pro L ys Pro Ala Ala Pro Asp
        35                  40                  45

Gly Thr Pro Ile Val Ser Ser Leu Pro Ile A sn Arg Arg Pro Arg Arg
    50                  55                  60

Asn Arg Arg Ser Ser Ala Ala Arg Ala Ala P he Gln Glu Thr Asn Ile
65                  70                  75                  80

Ser Pro Ala Asn Leu Val Tyr Pro Leu Phe I le His Glu Gly Glu Glu

-continued

```
                         85                  90                   95
Asp Thr Pro Ile Gly Ala Met Pro Gly Cys Tyr Arg Leu Gly Trp Arg
                100             105             110
His Gly Leu Val Glu Val Ala Lys Ala Arg Asp Val Gly Val Asn
        115             120             125
Ser Ile Val Leu Phe Pro Lys Val Pro Asp Ala Leu Lys Thr Ser Thr
    130             135             140
Gly Asp Glu Ala Tyr Asn Asp Asn Gly Leu Val Pro Arg Thr Ile Arg
145             150             155             160
Leu Leu Lys Asp Lys Tyr Pro Asp Leu Val Ile Tyr Thr Asp Val Ala
                165             170             175
Leu Asp Pro Tyr Ser Ser Asp Gly His Asp Gly Ile Val Arg Glu Asp
            180             185             190
Gly Val Ile Met Asn Asp Glu Thr Val His Gln Leu Cys Lys Gln Ala
            195             200             205
Val Ala Gln Ala Arg Ala Gly Ala Asp Val Val Ser Pro Ser Asp Met
        210             215             220
Met Asp Gly Arg Val Gly Ala Ile Arg Ala Ala Leu Asp Ala Glu Gly
225             230             235             240
Phe Gln His Val Ser Ile Met Ser Tyr Thr Ala Lys Tyr Ala Ser Ser
                245             250             255
Phe Tyr Gly Pro Phe Arg Glu Ala Leu Asp Ser Asn Pro Arg Phe Gly
            260             265             270
Asp Lys Lys Thr Tyr Gln Met Asn Pro Ala Asn Tyr Arg Glu Ala Leu
        275             280             285
Val Glu Met Gln Ala Asp Glu Ser Glu Gly Ala Asp Ile Leu Leu Val
    290             295             300
Lys Pro Gly Leu Pro Tyr Leu Asp Ile Ile Arg Leu Leu Arg Asp Lys
305             310             315             320
Ser Pro Leu Pro Ile Ala Ala Tyr Gln Val Ser Gly Glu Tyr Ser Met
                325             330             335
Ile Lys Ala Gly Gly Val Leu Lys Met Ile Asp Glu Glu Arg Val Met
            340             345             350
Met Glu Ser Leu Met Cys Leu Arg Arg Ala Gly Ala Asp Ile Ile Leu
        355             360             365
Thr Tyr Phe Ala Leu Gln Ala Gly Arg Cys Leu Cys Gly Glu Lys Arg
370             375             380
```